(12) United States Patent
Rogers et al.

(10) Patent No.: US 10,596,347 B2
(45) Date of Patent: Mar. 24, 2020

(54) LARGE LUMEN GUIDE CATHETER

(71) Applicant: Cardinal Health Switzerland 515 GMBH, Baar (CH)

(72) Inventors: Paul P Rogers, Miami, FL (US); M. Scott Jones, Livermore, CA (US); Nhut Diep, San Francisco, CA (US)

(73) Assignee: CARDINAL HEALTH SWITZERLAND 515 GMBH, Baar (CH)

( * ) Notice: Subject to any disclaimer, the term of this patent is extended or adjusted under 35 U.S.C. 154(b) by 800 days.

(21) Appl. No.: 15/316,910

(22) PCT Filed: May 19, 2014

(86) PCT No.: PCT/US2014/038570
§ 371 (c)(1),
(2) Date: Dec. 7, 2016

(87) PCT Pub. No.: WO2014/189828
PCT Pub. Date: Nov. 27, 2014

(65) Prior Publication Data
US 2017/0095640 A1    Apr. 6, 2017

Related U.S. Application Data

(60) Provisional application No. 61/825,089, filed on May 19, 2013, provisional application No. 61/825,481, filed on May 20, 2013.

(51) Int. Cl.
*A61M 25/00* (2006.01)
*A61M 25/06* (2006.01)

(52) U.S. Cl.
CPC ...... *A61M 25/005* (2013.01); *A61M 25/0012* (2013.01); *A61M 25/0662* (2013.01)

(58) Field of Classification Search
CPC ............ A61M 25/005; A61M 25/0662; A61M 25/0012
See application file for complete search history.

(56) References Cited

U.S. PATENT DOCUMENTS

| 5,071,407 A | 12/1991 | Termin et al. |
| 5,176,660 A | 1/1993 | Truckai |

(Continued)

FOREIGN PATENT DOCUMENTS

| CN | 101896217 A | 11/2010 |
| CN | 102029006 A | 4/2011 |

(Continued)

OTHER PUBLICATIONS

International Preliminary Report on Patentability for Application No. PCT/US2014/038570, dated Nov. 24, 2015, 10 pages.

(Continued)

*Primary Examiner* — Rebecca E Eisenberg
(74) *Attorney, Agent, or Firm* — McDonnell Boehnen Hulbert & Berghoff LLP

(57) ABSTRACT

A large lumen guide catheter (10) has an elongate tubular body (22), which has an outer surface (24), an inner surface (44), and a braided wire layer between the inner surface and the outer surface, wherein the wires winding a first helical direction are thicker and wider than the wire winding in a second helical direction opposite the first helical direction.

15 Claims, 8 Drawing Sheets

(56) References Cited

U.S. PATENT DOCUMENTS

| | | | |
|---|---|---|---|
| 5,891,112 A | 4/1999 | Samson | |
| 5,891,114 A | 4/1999 | Chien et al. | |
| 6,042,578 A | 3/2000 | Dinh et al. | |
| 6,689,120 B1 | 2/2004 | Gerdts | |
| 7,438,712 B2 | 10/2008 | Chouinard | |
| 2004/0143239 A1 | 7/2004 | Zhou et al. | |
| 2006/0229589 A1 | 10/2006 | Itou et al. | |
| 2012/0172798 A1* | 7/2012 | Miller | A61B 17/221 604/103.09 |

FOREIGN PATENT DOCUMENTS

| | | | |
|---|---|---|---|
| CN | 102300600 A | 12/2011 | |
| EP | 0732117 A2 | 9/1996 | |
| EP | 0839548 A1 | 5/1998 | |
| EP | 1712247 A1 | 10/2006 | |
| JP | H11155956 A | 6/1999 | |
| RU | 1812999 A3 | 4/1993 | |
| RU | 98115856 A | 6/2000 | |
| WO | 0137918 A1 | 5/2001 | |
| WO | 2011057131 A1 | 5/2011 | |

OTHER PUBLICATIONS

International Search Report and Written Opinion for Application No. PCT/US2014/038570, dated Aug. 28, 2014, 14 pages.
Examination Report for European Patent Application No. 14734595.3, dated Sep. 20, 2018, 5 pages.

\* cited by examiner

LARGE LUMEN GUIDE CATHETER

RELATED APPLICATIONS

This application claims the benefit of U.S. Provisional Patent Application Ser. No. 61/825,089, filed May 19, 2013, and of U.S. Provisional Patent Application Ser. No. 61/825,481, filed May 20, 2013, the entire disclosures of which are both incorporated by reference.

BACKGROUND

1. Technical Field

The invention relates to guide catheters.

2. Related Devices and Methods

A guide catheter serves to provide a lumen for the advancement therethrough of therapeutic devices, at least from an entry point to the vasculature to an ostium of a coronary artery. It is desirable that the proximal portion (closest to the physician along the longitudinal axis of the guide catheter) have stiffer properties than the distal portion (furthest from the physician, along the longitudinal axis of the guide catheter) to provide sufficient "pushability" and flexibility to advance the guide catheter, typically tracking along a guide wire, through the vasculature, to the desired site. Additional desirable properties of guide catheters are sufficient "back up support", which describes the ability of the guide catheter to provide an equal and opposing force to the therapeutic device therein and therefore resist movement of the guide catheter away from the ostium when the therapeutic device contacts the guide catheter under the force of trying to, for instance, advance across an occlusion or stenosed section of the coronary artery. Another is the ability to transmit torque from proximal end where the physician grips the hub and applies torque to the distal end, which the physician is trying to twist. The higher the torque transmission the better. However, transmitting torque without large torsional deflection, and the "whipping" that results when the physician twists the proximal handle of the guide catheter and the distal tip does not follow, but builds angular energy until it finally releases and the distal end "whips" through the twist angle should be avoided. The smaller of an angle a guide catheter "whips" through, the better. Another is the ability to avoid kinking, as kinking closes the lumen and may create difficulties in advancing or retrieving the guide catheter or therapeutic device therein. Typically kinking properties are described by the smallest radius that a section of the guiding catheter can assume without kinking. The smaller the radius, the more resistant to kinking the guide catheter is, meaning a greater chance of a successful procedure.

Braid reinforced guide catheters have been commercialized for many years for cardiovascular and endovascular procedures and stent delivery to provide thin walled tubular devices that permit either smaller outer diameters for the same sized inner diameter, or a larger inner diameter for the same sized outer diameter. After many years of competition and optimization of braid reinforced catheters, the largest diameter of an inner lumen on a 6 French guide catheter is marketed as 0.071 inches, in a product sold by Terumo, as well as Medtronic's LAUNCHER™ guide catheter. Most others on the market today have a 0.070 inch inner diameter for a 6 French guide catheter.

SUMMARY

A medical device comprising an elongate tubular body with an outer diameter of no more than 0.0835 inches (2.1209 mm), an inner diameter of no less than 0.0715 inches (1.8161 mm), a proximal end, a distal end, and a total length therebetween; and a sole reinforcement tubular structure embedded in polymer between the outer diameter and the inner diameter of the elongate tubular body from the proximal end of the elongate tubular body to proximal to the distal end of the elongate tubular body, the sole reinforcement tubular structure made solely of a first plurality of elongate wire ribbons and a second plurality of elongate wire members braided together in a braid configuration; wherein each of the first plurality of elongate wire members arranged in a counter-clockwise helix about a central longitudinal axis of the elongate tubular body and having a first constant transverse cross-sectional shape, which first cross-sectional shape has a maximum thickness and a maximum width, the maximum width being at least three times as great as the maximum thickness and no more than four and a half times as great as the maximum thickness; and each of the second plurality of elongate wire members arranged in a clockwise helix about the central longitudinal axis of the elongate tubular body and having a second constant transverse cross-sectional shape, which second cross-sectional shape has a maximum thickness and a maximum width, the maximum width being at least two times a great as the maximum thickness and no more than three times as great as the maximum thickness.

A medical device comprising an elongate tubular body with an outer diameter of no more than 0.0835 inches (2.1209 mm), an inner diameter of no less than 0.0720 inches (1.8288 mm), a proximal end, a distal end, and a total length therebetween; and a sole reinforcement tubular structure embedded in polymer between the outer diameter and the inner diameter of the elongate tubular body from the proximal end of the elongate tubular body to proximal to the distal end of the elongate tubular body, the sole reinforcement tubular structure made solely of a first plurality of elongate wire ribbons and a second plurality of elongate wire members braided together in a braid configuration; wherein each of the first plurality of elongate wire members arranged in a counter-clockwise helix about a central longitudinal axis of the elongate tubular body and having a first constant transverse cross-sectional shape, which first cross-sectional shape has a maximum thickness and a maximum width, the maximum width being at least three times as great as the maximum thickness and no more than four and a half times as great as the maximum thickness; and each of the second plurality of elongate wire members arranged in a clockwise helix about the central longitudinal axis of the elongate tubular body and having a second constant transverse cross-sectional shape, which second cross-sectional shape has a maximum thickness and a maximum width, the maximum width being at least two times a great as the maximum thickness and no more than three times as great as the maximum thickness.

A medical device comprising: an elongate tubular body having a first total length, a proximal end, a distal and, a central longitudinal axis and a lumen therethrough, and consisting of: an innermost polymeric tubular layer having a second total length, a proximal end, and a distal end; an outermost polymeric tubular layer having a third total length, a proximal end, and a distal end; and a braided reinforcement layer wholly embedded in one or more of the inner and outer polymeric tubular layers, and having a fourth total length, a proximal end, and a distal end; wherein the braided reinforcement layer consists of 16 wire members, braided in a 2-over, 2-under pattern, where 8 of the 16 wire members have transverse cross-sectional rectangular shape having a 0.002 inch thickness and a 0.005 inch width, and the other 8 of the 16 wire members have a transverse cross-sectional rectangular shape having a 0.001 inch thickness and a 0.004 inch width.

These and other features, benefits, and advantages of the present invention will be made apparent with reference to the following detailed description, appended claims, and accompanying figures, wherein like reference numerals refer to structures that are either the same structures, or perform the same functions as other structures, across the several views.

BRIEF DESCRIPTION OF THE FIGURES

The figures are merely exemplary and are not meant to limit the present invention.

DETAILED DESCRIPTION

Figure 1:
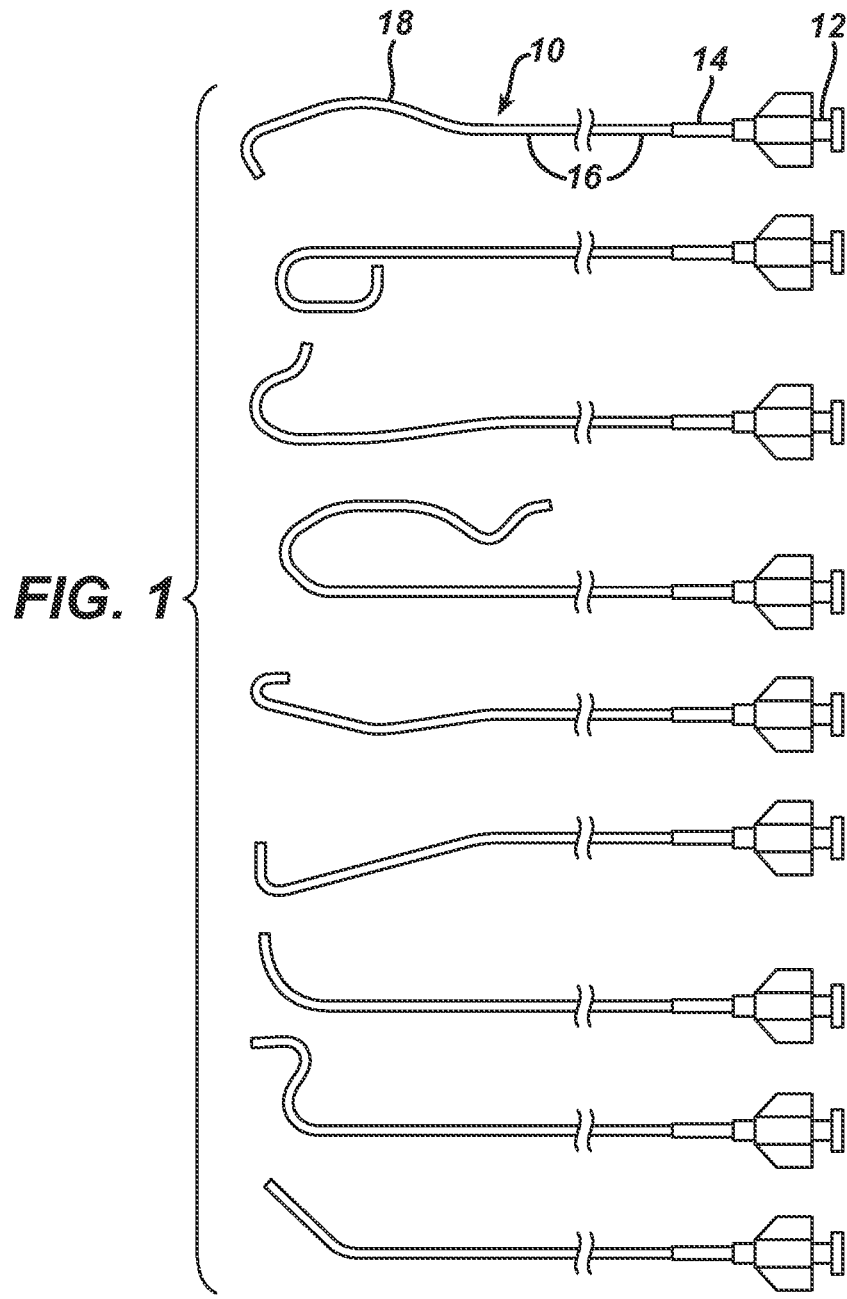
FIG. 1 illustrates guiding catheters in accordance with the invention.

The guide catheters shown in FIG. 1 have useful application as a guiding catheter for guiding a therapeutic device, for example, a dilation catheter for PTCA (balloon catheter), a stent delivery system, or a drug coated balloon catheter, or the like to a target location such as a stenosed portion of a coronary artery. Each guiding catheter 10 has a proximal hub 12, a strain relief 14 co-axial with the main catheter body 16, which is visible in FIG. 1 extending to the left of strain relief 14, although the total length of main catheter body 16 is not displayed, the relevant distal portions 18 of each guiding catheter assume a pre-formed shape when not under external forces. These distal portions "straighten" as they are introduced to and advanced through the vascular system over a guidewire, and regain their pre-formed shape when the placement guide wire is withdrawn proximally from at least the distal portion. Once the distal portion returns to the pre-formed shape, advancing the guidewire distally therethrough does not straighten the guide catheter, but instead, the guide wire conforms to the curves of the lumen of the guide catheter.

Figure 2:
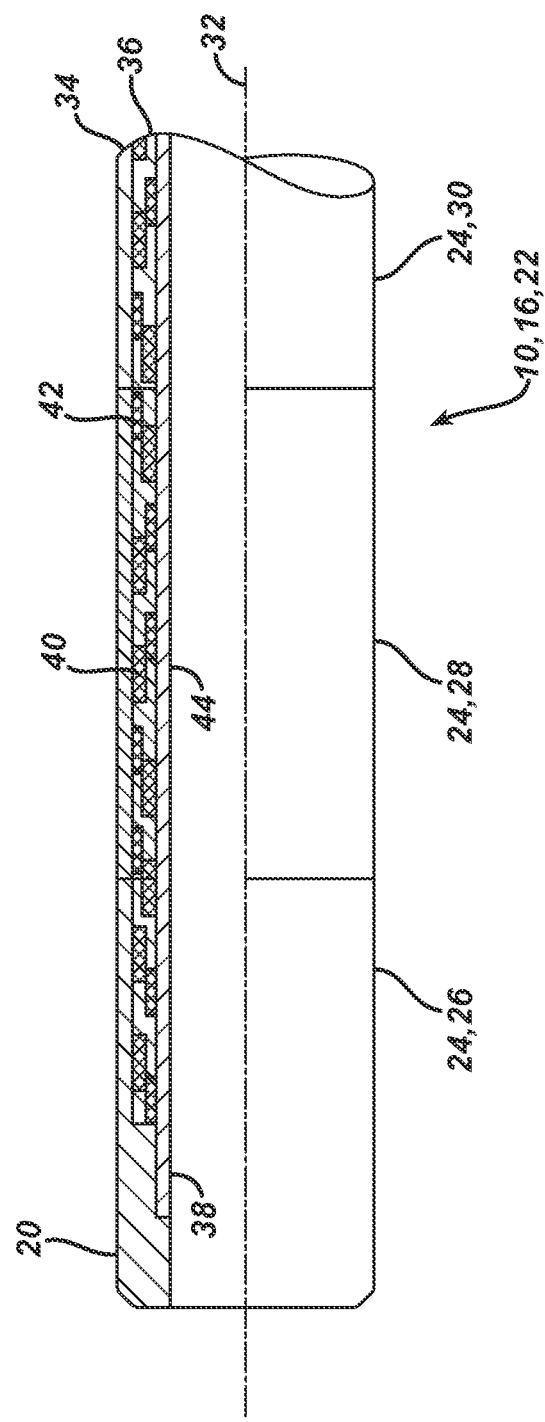
FIG. 2 illustrates a partial cross-sectional view along a plane containing the central longitudinal axis of a distal portion of a guiding catheter in accordance with the invention, including a braidless distal end.

Turning to FIG. 2, a guide catheter 10 in accordance with the invention may include a braidless tip 20 that exhibits relatively high flexibility and is mounted on the distal side or distal end of the catheter main body 16. The catheter main body 16 is an elongate tubular body 22, a distal portion of which is shown in partial longitudinal cross-section in FIG. 2. Elongate tubular body 22 has an outer surface 24, comprised of a first region 26, a second region 28 proximally abutting the first region 26, a third region 30 proximally abutting the second region 28, a fourth region (not shown) proximally abutting the third region 30, and a fifth region (not shown) proximally abutting the fourth region. The third region 30 is made of a material having a lower durometer, and is more flexible than the fourth region, the second region 28 is made of a material having a lower durometer, and is more flexible than the third region 30, and the first region 26 is made of a material having a lower durometer, and is more flexible the second region 28. Accordingly, the elongate tubular body 10 may gradually increase in flexibility along the distal direction along the longitudinal axis 32. In certain embodiments, the material of region 26 is the same material as region 28, even though assembled as a separate member initially.

Except for braidless tip 20, elongate tubular body 22 has three layers, and outer layer 34, a braided layer 36, and an inner layer 38. Outer layer 34 comprises the series of materials selected for the various regions, discussed above, and in any one region, the material constituting the outer layer may be a polyamide based material, such as Nylon or PEBAX, a blend thereof, or a polyurethane, such as Pellathane. The material constituting the inner layer 38 is a lubricious polymer, such as polytetrafluoroethylene ("PTFE"), or high density polyethylene (HDPE).

Braidless tip 20 may be constructed completely from one material, or it may be a composite structure as shown in FIG. 2. In FIG. 2, braidless distal tip is formed from the distal extension of the polymer forming the outer layer of elongate tubular body region 26, except for its proximal and inner surface, which is formed from the distal extension of the lubricious polymer forming the inner layer 38.

Returning to the construction of elongate tubular body 22, the braided layer comprises a first plurality of elongate wire members winding in a clockwise direction about longitudinal axis 32 and a second plurality of elongate wire members winding in a counterclockwise direction about longitudinal axis 32. Elongate wire member 40 is one of the first plurality of elongate wire members and elongate wire member 442 is one of the second plurality of elongate wire members. The first plurality and the second plurality of wires that form the braided layer are embedded in polymer between outer surface 24 and inner surface 44. Preferably, they are embedded in the polymer forming outer layer 34 and outer surface 24. Thus, braid layer 36 overlaps in space with at least outer layer 34. Braided layer 36 forms the sole reinforcement structure in elongate tubular body 22. There are no other reinforcing structures, such as fibers running generally parallel ("straight") to longitudinal axis 32.

Figure 3:
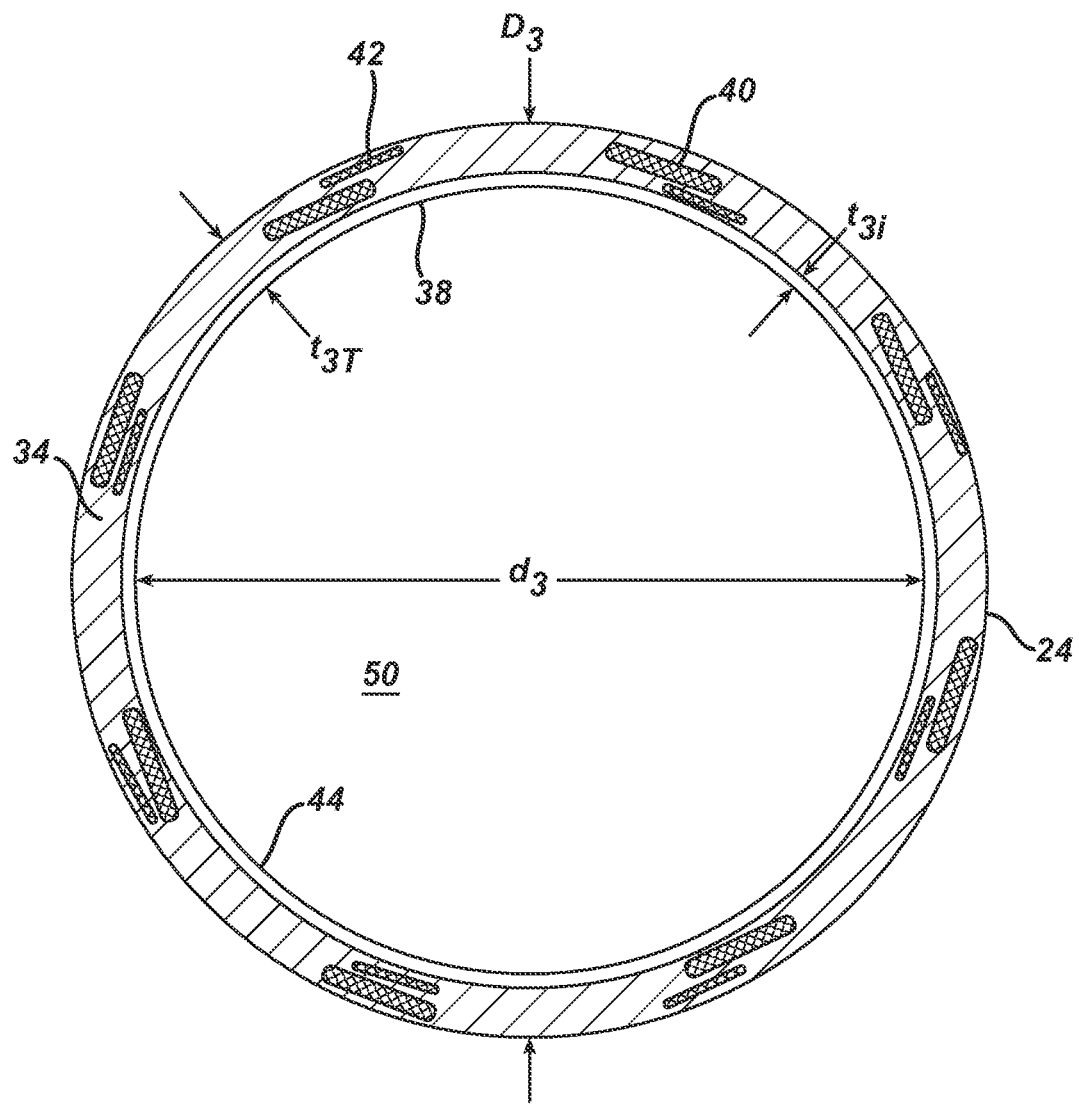
FIG. 3 is a copy of a photograph of a transverse cross-section of a guiding catheter in accordance with the invention.

FIG. 3 is a copy of a photograph of a magnified transverse cross-section of an elongate tubular body with a first plurality of elongate wire members and a second plurality of elongate wire members. In this embodiment, there are sixteen elongate wire members total, with eight forming the first plurality and eight forming the second plurality. For ease of depiction, only one of each plurality has been labeled in FIG. 3. Also labeled on FIG. 3 are the inner diameter, $d_3$, outer diameter, $D_3$, lumen 50, outer layer 34, outer surface 24, overall wall thickness, $t_{3T}$, wall thickness of inner layer 38, and $t_{3i}$. FIG. 3 depicts a cross section where the elongate wire members of the first plurality of elongate wire members cross the elongate wire members of the second plurality of elongate wire members. The braid pattern in this embodiment is such that in every other location around the annular cross-section of elongate tubular body 22, as elongate wire member of the first plurality of elongate wire members is located "over" an elongate wire member of the second plurality of elongate wire members, and in the remaining locations, an elongate wire member of the first plurality of elongate wire members is "under" an elongate wire member of the second plurality of elongate wire members. It should be noted that the cross-sectional areas of the elongate wire members are greater than their respective transverse cross-sectional area, due to the braid angle, which can be calculated knowing the number of elongate wire members used in the braid, the pics per inch, and the arrangement of elongate wires about the annulus, and the diameter of the braided layer.

Figure 4:
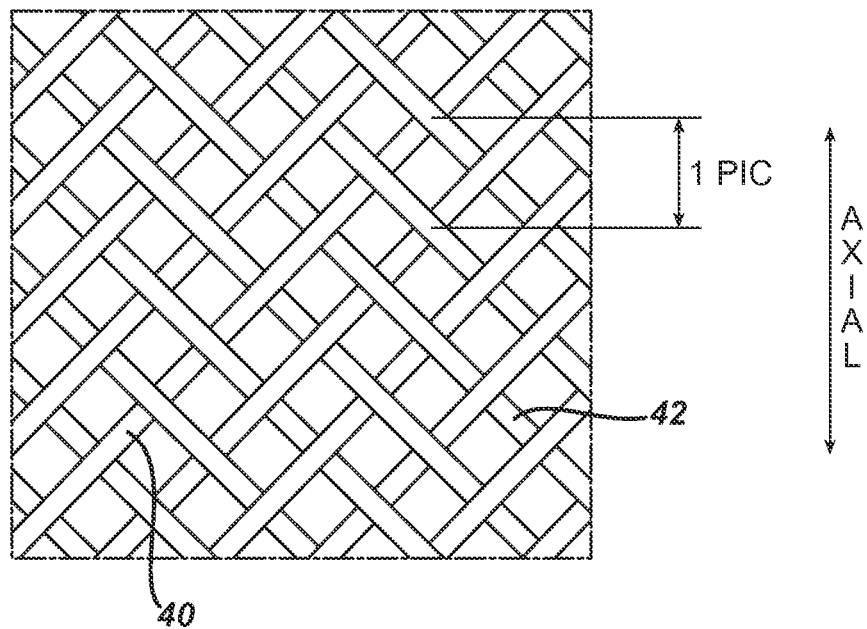
FIG. 4 illustrates a braid configuration of 1-over, 1-under.

FIG. 4 illustrates a first plurality of elongate wire members braided with a second plurality of elongate wire members in a 1-over, 1-under braid configuration. The distance between center-crossing points in two axially aligned sets of crossed wires is defined as a "pic", and informs the expression, PPI, pics per inch.

Figure 5:
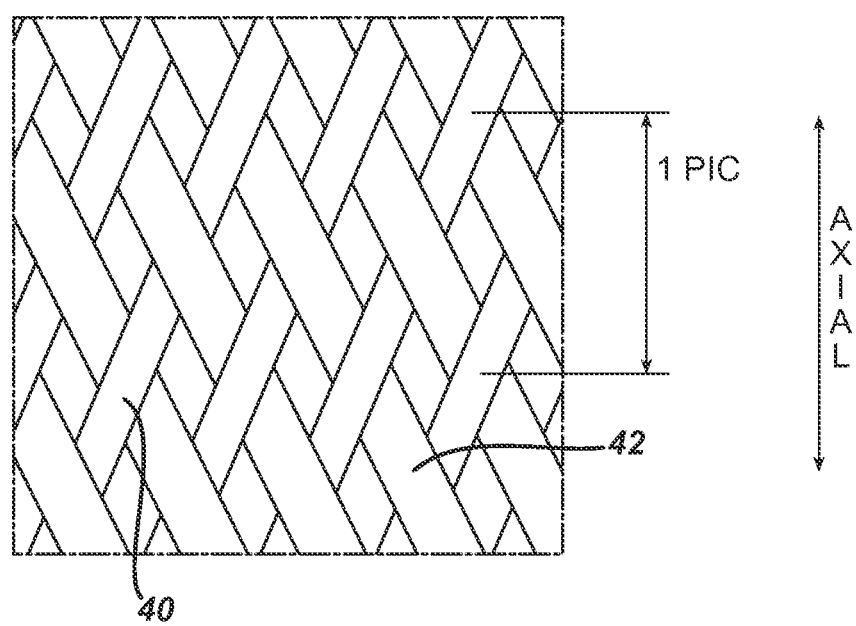
FIG. 5 illustrates a braid configuration of 2-over, 2-under.

FIG. 5 illustrates a first plurality of elongate wire members braided with a second plurality of elongate wire members in a 2-over, 2-under braid configuration.

Figure 6:
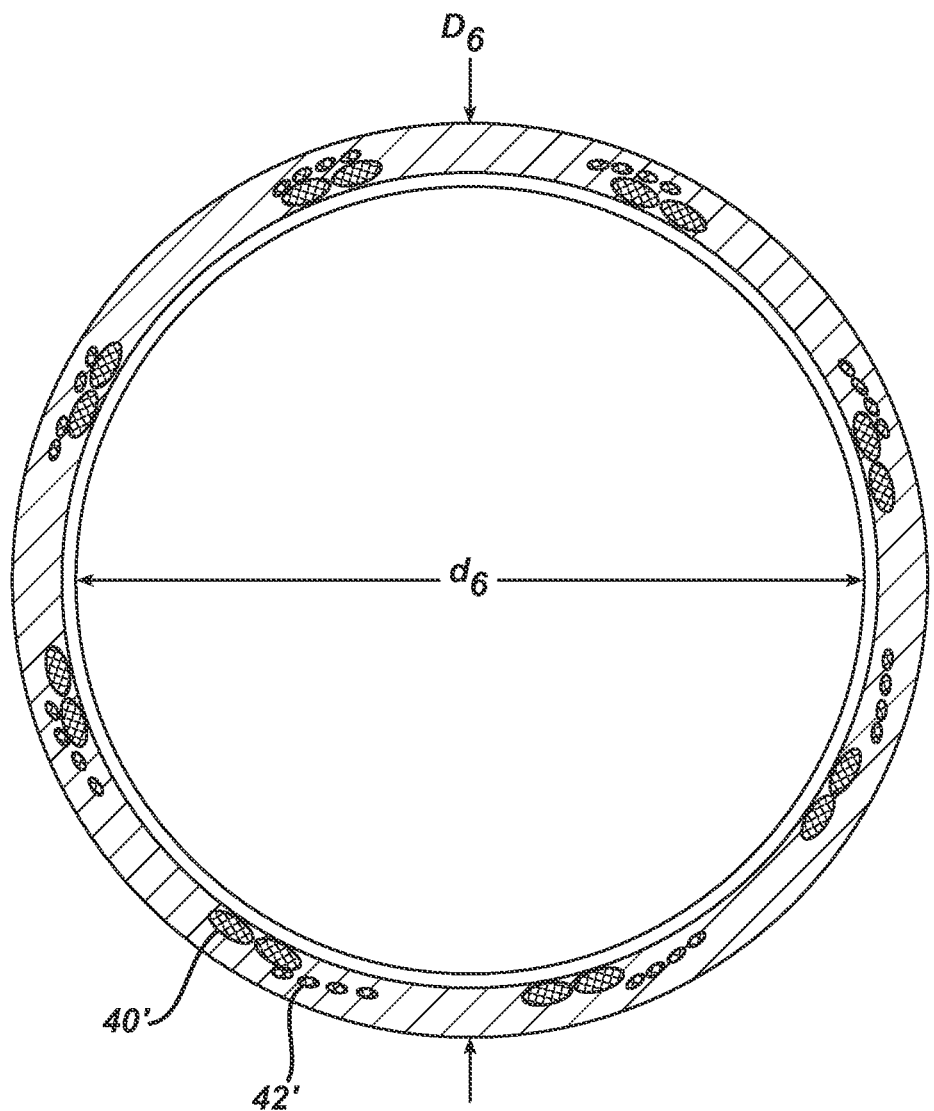
FIG. 6 illustrates a transverse cross-section of a first prior art guiding catheter at the same magnification as FIG. 3.

FIG. 6 is a copy of a photograph of a magnified transverse cross-section of an elongate tubular body with a first plurality of elongate wire members and a second plurality of elongate wire members. In this embodiment, there are forty-eight elongate wire members total, with thirty-two forming the first plurality and sixteen forming the second plurality. The thirty-two of the first plurality are grouped in sub sets of four, generally round cross-sectionally shaped small elongate wire members in the place of one "flat" (rectangular cross-section) wire ribbon having a width equal to the sum of the four diameters, and a thickness equal to the diameter of the elongate wire members. (It is again noted that the cross-sectional shapes in the photograph are not round due to the braid angle.) The sixteen second plurality of elongate wire members in are grouped in subsets of two, generally round cross-sectionally shaped elongate wire members in the place of one "flat" (rectangular cross-section) wire ribbon, where these two elongate wire members, each appear to be twice as large in diameter as one of the thirty-two elongate wire members of the first plurality. For ease of depiction, only one of each plurality has been labeled in FIG. 6. Also labeled on FIG. 6 are the inner diameter, d.sub.3, outer diameter, D.sub.3, lumen 50, outer layer 34, outer surface 24, overall wall thickness, t.sub.3T, wall thickness of inner layer 38, and t.sub.3i.

Figure 7:
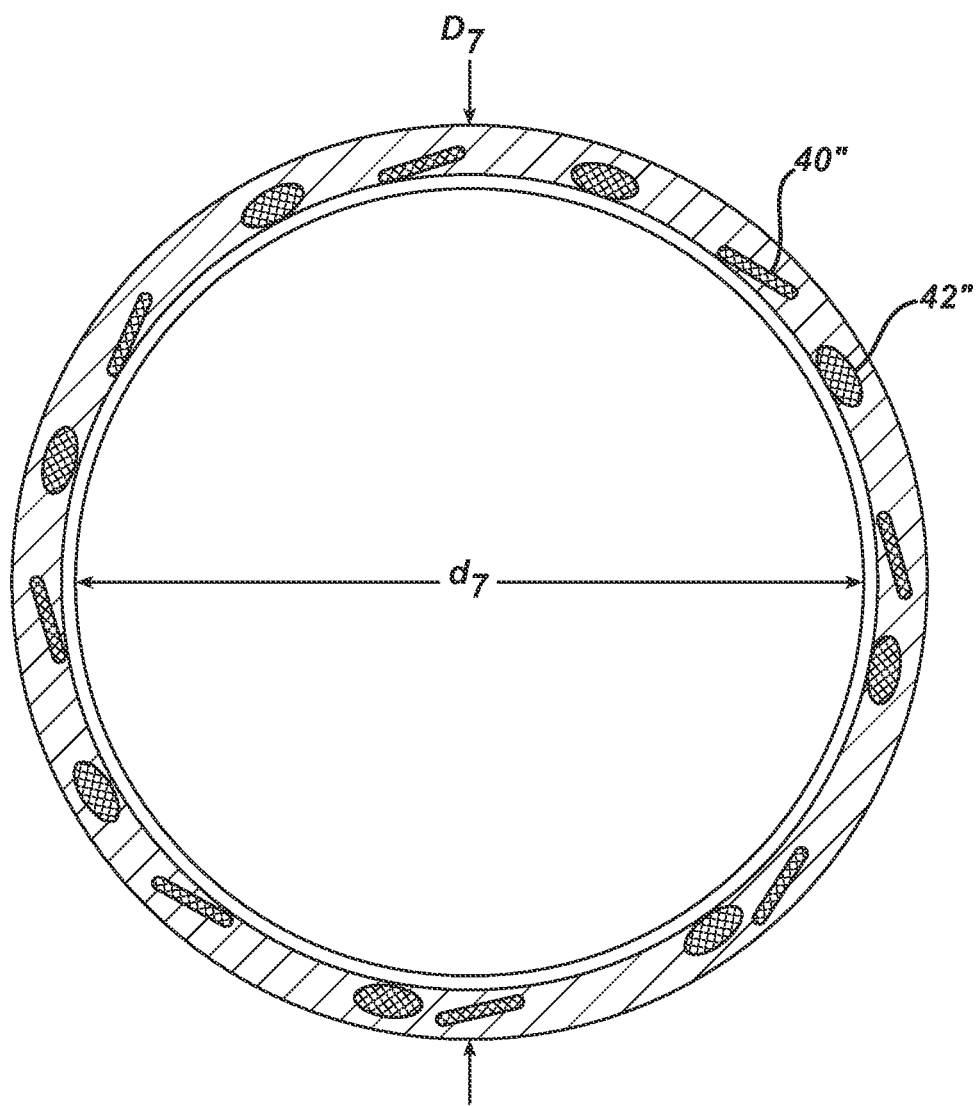
FIG. 7 is a copy of a photograph of a transverse cross-section of a second prior art guiding catheter at the same magnification as FIG. 3.
Figure 8:
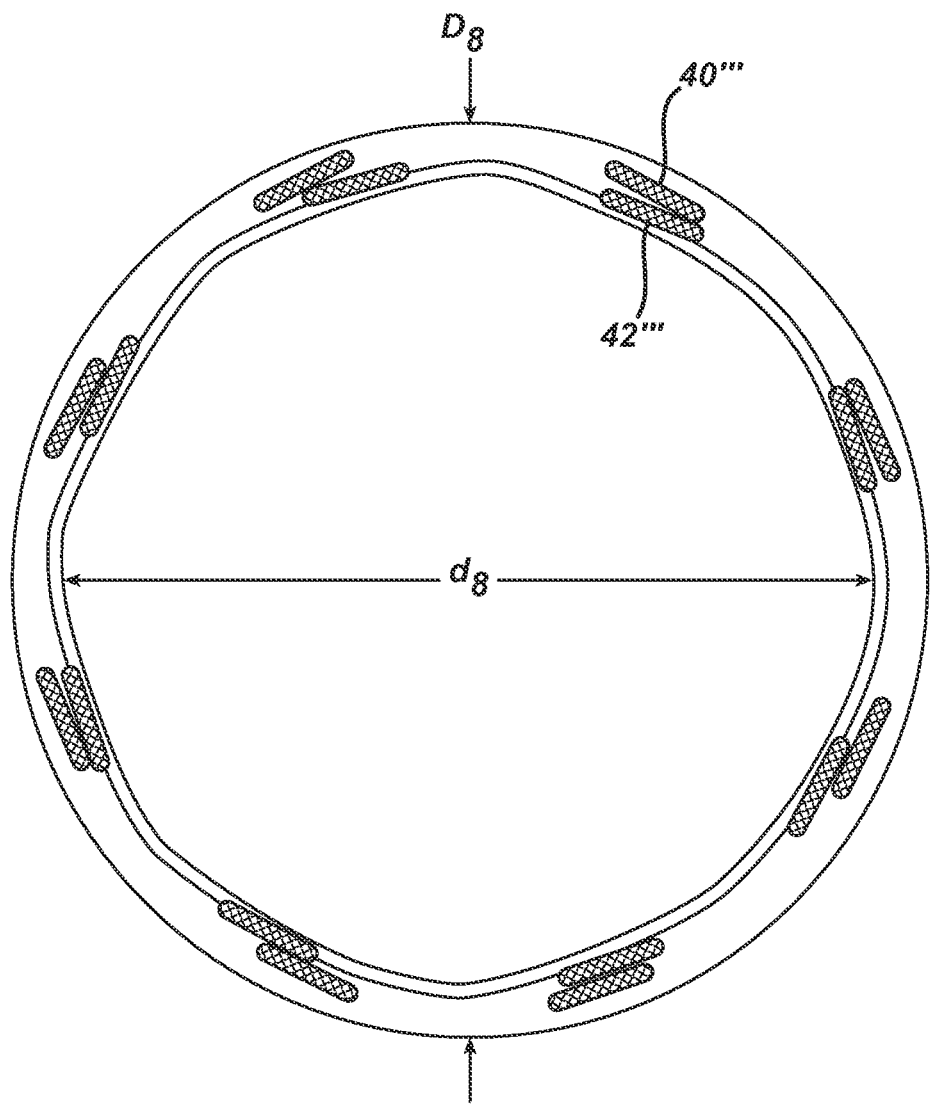
FIG. 8 is a copy of a photograph of a transverse cross-section of a third prior art guiding catheter at the same magnification as FIG. 3.
Figure 9:
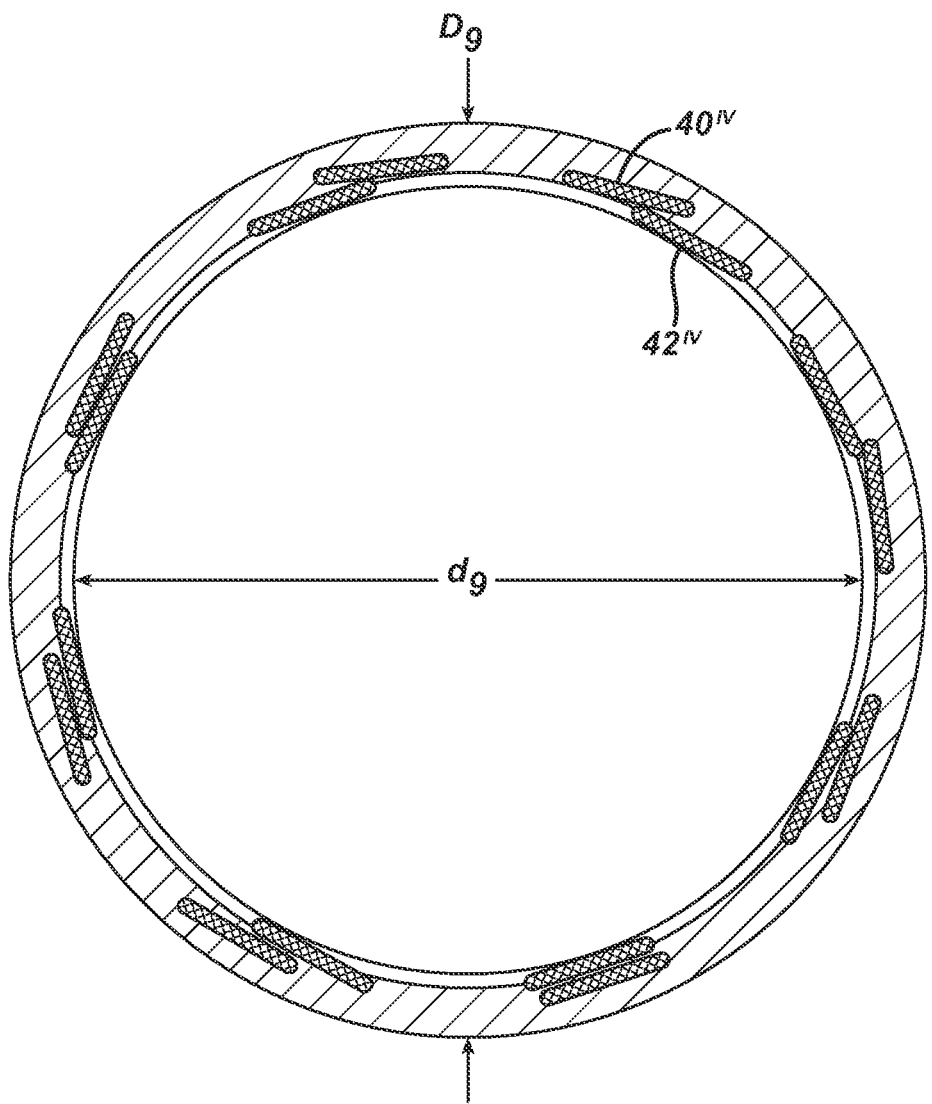
FIG. 9 is a copy of a photograph of a transverse cross-section of a fourth prior art guiding catheter at the same magnification as FIG. 3.

FIGS. 7, 8, and 9 are copies of photographs of a magnified transverse cross-section of an elongate tubular body with a first plurality of elongate wire members and a second plurality of elongate wire members, where the magnification for each is the same as in FIG. 3. In each prior art catheter, there are sixteen elongate wire members total, with eight forming the first plurality and eight forming the second plurality. For ease of depiction, only one of each plurality has been labeled in the respective FIG. Also labeled on each respective FIG. are the inner diameter, d.sub.3, outer diameter, D.sub.3, lumen 50, outer layer 34, outer surface 24, overall wall thickness, t.sub.3T, wall thickness of inner layer 38, and t.sub.3i. The catheter of FIG. 7 has a plurality of elongate wire members with a rectangular transverse cross-sectional shape and a second plurality of elongate wire members with a circular transverse cross-sectional shape. The catheters of FIGS. 8 & 9 each have a first plurality of elongate wire members with a rectangular transverse cross-sectional shape and a second plurality of elongate wire members with a rectangular transverse cross-sectional shape. It appears in FIG. 8 that the dimensions of the members of the first plurality are the same as the dimensions of the members of the second plurality. The catheter of FIG. 8 is Medtronic's LAUNCHER™ guide catheter.

| Catheter of FIG. | Outer Diameter, D (inches) | Inner Diameter, d (inches) | 1$^{st}$ width (inches) | 1$^{st}$ thickness (inches) | 2$^{nd}$ width (inches) | 2$^{nd}$ thickness (inches) |
|---|---|---|---|---|---|---|
| 3 | 0.0835 | 0.072 | 0.004 | 0.001 | 0.005 | 0.002 |
| 6 | 0.0835 | 0.070 | * (diameter) | * (diameter) | 2* (diameter) | 2* (diameter) |
| 7 | 0.0835 | 0.070 | 0.003 | 0.001 | 0.0025 (diameter) | 0.0025 (diameter) |
| 8 | 0.0835 | 0.071 | 8W | 8T | 8W | 8T |
| 9 | 0.0835 | 0.071 | 9W | 9T | 9W | 9T |

SUMMARY TABLE WITH DIMENSIONS

In certain embodiments, the braid ppi is constant over the total length of the elongate tubular body. In certain embodiments, the braid ppi varies over the total length of the elongate tubular body. It should be understood that differences in ppi due to a manufacturing process window are considered insignificant and the resulting ppi is considered constant.

In certain embodiments, the braid ppi is constant and is a value between 60-70 ppi. In certain embodiments, the braid ppi is constant and is a value between 65-75 ppi. In certain embodiments, the braid ppi is constant and is a value between 60-90 ppi.

In certain embodiments, the braid ppi varies along the catheter, in an increasing fashion along longitudinal axis 32, the specific values falling between 60 and 90 ppi.

In certain embodiments, a 6 French guide catheter with a 0.072" inner diameter and a 0.0835" outer diameter, essentially constant over the length of the guide catheter. Except for the distal-most portion, there are three layers to the guide catheter: an outer tubular polymeric layer in four (or five) axial length sections, an inner tubular polymeric layer, and an intermediate tubular braided layer. The braided layer is embedded in the outer tubular layer.

In certain embodiments, the inner tubular polymeric layer is made of PTFE without radiopaque material.

In certain embodiments, the braided tubular reinforcement structure has 16 stainless steel ribbons evenly spaced about the circumference, 8 winding helically about the inner layer in a clockwise direction, and 8 winding helically about the inner layer in a counterclockwise direction, and the 16 ribbons are braided in a 2-over, 2-under-pattern with 70+/−3 pics per inch, which is constant along the entire length of the braided layer. The counterclockwise ribbons each have a rectangular transverse cross-section with a 0.002" thickness and 0.005" width, oriented with respect to the inner tubular layer such that the width is normal to the radial direction and the thickness is in the radial direction. The clockwise ribbons each have a rectangular transverse cross-section having a 0.001" thickness and a 0.004" width, oriented with respect to the inner tubular layer such that the width is normal to the radial direction and the thickness is in the radial direction.

In certain embodiments, the outer tubular polymer layer comprises four separate tubular sections that abut each other and are individually made of blends of nylon 12 and a polyetherblockamide. The four sections have sequentially decreasing durometer, but all are higher (Shore D scale) than the Shore A 80 durometer of the distal tip.

In certain embodiments, the outer tubular polymer layer has a fifth outer tubular polymer layer that is distal to the four other sections and proximal to (and abutting) the distal tip. This fifth section is made of the same material as the distal tip.

In certain embodiments, the distal tip is made of a urethane, sold as Pellethane 80AE, with radiopaque filler (bismuth trioxide). Pellethane 80AE has a hardness measured on the Shore A scale of 80.

In certain embodiments, the inner tubular polymeric layer is the longest of the three layers. The distal end of the braided layer is proximal to the distal end of the inner tubular polymeric layer. The distal end of the fourth (or fifth, if any) outer tubular polymeric layer section is proximal to the distal end of the braided layer. The distal tip extends proximally to abut the distal most outer polymeric layer section and the braided layer is embedded in the distal tip material. Distal to the distal end of the braided layer, there are only two layers, the distal tip material being the outer layer and the PTFE liner being the inner layer. The remaining distance of the distal end of the guide catheter is comprised completely and only of the distal tip material, and has the same OD (0.0835") and ID (0.072") of the remainder of the main catheter body, or elongate tubular body.

In certain embodiments, the outer surface of the inner layer is chemically etched to assist in a mechanical bond between it and various outer tubular layers. The distal tip and all components are assembled over a metal mandrel and encased in a heat-shrink tube and heated to bond all adjoining polymeric surfaces and to embed the braided layer in the respective outer layer material. After bonding, the heat shrink tube is slit longitudinally and peeled from the guide catheter, and the outer diameter of the distal tip is ground down to size.

In certain embodiments, the outer layer may be extruded onto the braided layer over the inner layer, and then ground down for the areas where different durometer tubular sections may be assembled and bonded.

Comparisons

The following tables show comparisons between the prior art catheter shown in FIG. 8 and an embodiment in accordance with the invention.

EXAMPLE 1

An embodiment in accordance with the invention has an outer diameter of 0.0835 inches and an inner diameter of 0.0720 inches, a braid pattern of 2-over, 2 under, at a ppi of 70. There are sixteen flat wires all with a rectangular cross-section. The dimensions of the first transverse cross-sectional shape

COMPARATIVE EXAMPLE 1

Catheter of FIG. 8 has an outer diameter of 0.0835 inches and an inner diameter of 0.0710 inches (although it really looks more polygonal than circular), has a braid pattern of 2-over, 2-under, at a ppi of approximately 63. There are sixteen flat wires all with a rectangular cross-section and equal dimensions. It is believed that the dimensions of the transverse cross-section of each of the 16 wires are 0.004 inches wide by 0.0015 inches thick. It is sold by Medtronic under the brand name LAUNCHER™.

In Table 2 below, three Medtronic LAUNCHER™ guide catheters and three catheters of EXAMPLE 1 were tested to determine the maximum backup force they would provide without moving out of the target location (in intended use, an ostium of a coronary artery). The results show that even though the catheters of EXAMPLE 1 have a thinner wall, they provide greater support to therapeutic catheters exerting forces on them, as the therapeutic catheters are urged across stenosed regions of the coronary artery.

TABLE 2

| Group | Sample | time | Max. Backup Force (g), t = 0 |
|---|---|---|---|
| COMP. EX. 1 | S1 | 0 min | 178.3783 |
| COMP. EX. 1 | S2 | 0 min | 168.0737 |
| COMP. EX. 1 | S3 | 0 min | 171.4017 |
| EXAMPLE 1 | S1 | 0 min | 219.2893 |
| EXAMPLE 1 | S2 | 0 min | 187.5608 |
| EXAMPLE 1 | S3 | 0 min | 226.9528 |
| Average | | | |
| EXAMPLE 1 | 211.2676 | | |
| Medtronic LAUNCHER ® | 172.6179 | | |

In Table 3 below, three catheters of Comparative example 1 and three catheters of Example 1 were tested to determine the torque required to twist the catheter's proximal handle, either clockwise ("CW") or counter-clockwise ("CCW") when the distal tip is held motionless, before the catheter kinks. In practice, physicians rarely twist a guide catheter's proximal handle more than 1.5 turns (540 degrees) without seeing the distal dip move. The data below is the torque required to twist the proximal handle 360 degrees relative to the distal tip. Higher values are better, as a stronger structure resists the twist with a greater force.

TABLE 3

| Group | Sample | Torque to 360 CW (ounce-inches) | Torque to 360 CCW (ounce-inches) |
|---|---|---|---|
| COMP. EX. 1 | S1 | 2.55 | 2.65 |
| COMP. EX. 1 | S2 | 2.7 | 2.45 |
| COMP. EX. 1 | S3 | 2.45 | 2.5 |
| EXAMPLE 1 | S1 | 2.6 | 2.9 |
| EXAMPLE 1 | S2 | 2.65 | 2.85 |
| EXAMPLE 1 | S3 | 2.65 | 2.8 |
| Average | | | |

TABLE 3-continued

| Group | Torque to 360 CW (ounce-inches) | Torque to 360 CCW (ounce-inches) |
|---|---|---|
| EXAMPLE 1 | 2.85 oz-in. | |
| Medtronic LAUNCHER ® | 2.53333 oz-in. | |

In Table 4 below, two catheters of Example 1 and two catheters of Comparative example 1 were tested to determine the percent "whip" of the distal tip in 37 degrees Fahrenheit water when tested when first put into the water (t=0 minutes) and after 5 minutes (t=5 minutes). In this test, the catheter is in a U shaped arch made to model the aortic arch, and the hub is turned at a constant low speed (revolution per minute) for a set period of time (here enough time to complete five revolutions of the proximal hub). The distal end of the guide catheter is unconstrained (other than being in a larger tubular "U", and thus facing 180 degrees opposite to the proximal hub. The rotation of the distal end is tracked and the two rotations are plotted against one another (proximal input versus distal output). When "whip" occurs, the distal tip rotates a large amount for a small given input rotation. The reported numbers indicate the percent of the time tested during which the distal end was "whipping". Lower percentage "whip" is better.

TABLE 4

| Group | Rotation | Sample | Time (minutes) | Whip |
|---|---|---|---|---|
| COMP. Ex. 1 | CCW | 1 | 0 | 23 |
| COMP. Ex. 1 | CCW | 2 | 0 | 23 |
| COMP. Ex. 1 | CCW | 1 | 5 | 34.6 |
| COMP. Ex. 1 | CCW | 2 | 5 | 34.4 |
| EXAMPLE 1 | CCW | 1 | 0 | 5 |
| EXAMPLE 1 | CCW | 2 | 0 | 4 |
| EXAMPLE 1 | CCW | 1 | 5 | 7.4 |
| EXAMPLE 1 | CCW | 2 | 5 | 13 |
| Average | | | | |
| EXAMPLE 1 | 7.35 | | | |
| Medtronic LAUNCHER ® | 28.75 | | | |

In Table 5 below, 6 catheters of Comparative Example 1 were compared to 3 catheter of Example 1 in determining the smallest bending radius before kinking of the elongate tubular bodies. Results show that Example 1 has a smaller bending radius, and therefore, surprising resists kinking better than Comparative Example 1.

TABLE 5

| Run | Segment | Kink Radius (mm) |
|---|---|---|
| COMP. Ex. 1 | Body | 4.68846 |
| COMP. Ex. 1 | Body | 4.6392 |
| COMP. Ex. 1 | Body | 4.61731 |
| COMP. Ex. 1 | Body | 4.68969 |
| COMP. Ex. 1 | Body | 4.94188 |
| COMP. Ex. 1 | Body | 4.86646 |
| EXAMPLE 1 | Body | 4.07229 |
| EXAMPLE 1 | Body | 4.01941 |
| EXAMPLE 1 | Body | 3.85478 |
| Average Kink Radius (mm) | | |
| EXAMPLE 1 | 3.98216 | |
| Medtronic LAUNCHER ® | 4.7405 | |

The present invention is not limited to the details of the above-described examples and embodiments. The scope of the invention is defined by the appended claims and all changes, modifications, and equivalents falling within the scope of the claims are encompassed by the claims.

The invention claimed is:

1. A guide catheter comprising:
   an elongate tubular body with an outer diameter of no more than 0.0835 inches (2.1209 mm), an inner diameter of no less than 0.0715 inches (1.8161 mm), a proximal end, a distal end, and a total length therebetween; and
   a sole reinforcement tubular structure embedded in polymer between the outer diameter and the inner diameter of the elongate tubular body from the proximal end of the elongate tubular body to proximal to the distal end of the elongate tubular body, the sole reinforcement tubular structure made solely of a first plurality of elongate wire members and a second plurality of elongate wire members braided together in a braid configuration;
   wherein each of the first plurality of elongate wire members arranged in a counterclockwise helix about a central longitudinal axis of the elongate tubular body and having a first constant transverse cross-sectional shape, which first cross-sectional shape has a maximum thickness and a maximum width, the maximum width being at least three times as great as the maximum thickness and no more than four and a half times as great as the maximum thickness; and
   each of the second plurality of elongate wire members arranged in a clockwise helix about the central longitudinal axis of the elongate tubular body and having a second constant transverse cross-sectional shape, which second cross-sectional shape has a maximum thickness and a maximum width, the maximum width being at least two times a great as the maximum thickness and no more than three times as great as the maximum thickness;
   wherein the braid configuration is 2-over, 2-under;
   wherein the first plurality of elongate wire members comprises eight wire members and the second plurality of elongate wire members comprises eight wire members; and
   wherein a braid pics per inch (ppi) is constant and is a value between 65 and 75 ppi.

2. The guide catheter of claim 1, wherein the elongate tubular body has an inner diameter of no less than 0.072 inches (1.8288 mm).

3. The guide catheter of claim 1, wherein the maximum width of the first cross-sectional shape is at least three times as great and no more than four times as great as the maximum thickness of the first cross-sectional shape.

4. The guide catheter of claim 1, wherein the maximum width of the first cross-sectional shape is three times as great as the maximum thickness of the first cross-sectional shape.

5. The guide catheter of claim 1, wherein the maximum width of the first cross-sectional shape is 0.003 inches.

6. The guide catheter of claim 1, wherein the maximum width of the first cross-sectional shape is four times as great as the maximum thickness of the first cross-sectional shape.

7. The guide catheter of claim 1, wherein the maximum width of first cross-sectional shape is 0.004 inches.

8. The guide catheter of claim 1, wherein the maximum width of the second cross-sectional shape is two and a half times as great as the maximum thickness of the second cross-sectional shape.

9. The guide catheter of claim 1, wherein the maximum width of the second cross-sectional shape is 0.005 inches.

10. The guide catheter of claim 1, wherein the first cross-sectional shape is selected from the group consisting of rectangular, oval, and elliptoid.

11. The guide catheter of claim 10, wherein the first cross-sectional shape is rectangular.

12. The guide catheter of claim 1, wherein the second cross-sectional shape is selected from the group consisting of rectangular, oval, and elliptoid.

13. The guide catheter of claim 12, wherein the second cross-sectional shape is rectangular.

14. The guide catheter of claim 1, wherein the polymer forming the outer diameter of the elongate tubular body comprises polyamide.

15. The guide catheter of claim 1, wherein the hardness of the polymer forming the outer diameter of the elongate tubular body has different values.

* * * * *